(12) United States Patent
Lin et al.

(10) Patent No.: US 12,370,084 B2
(45) Date of Patent: Jul. 29, 2025

(54) SYSTEM AND METHOD FOR EFFECTING WATER HAMMER IN SURGICAL SYSTEMS

(71) Applicant: JOHNSON & JOHNSON SURGICAL VISION, INC., Santa Ana, CA (US)

(72) Inventors: Justin Lin, Tustin, CA (US); Lauren Hickey, Irvine, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 787 days.

(21) Appl. No.: 17/447,672

(22) Filed: Sep. 14, 2021

(65) Prior Publication Data

US 2022/0079809 A1    Mar. 17, 2022

Related U.S. Application Data

(60) Provisional application No. 63/078,830, filed on Sep. 15, 2020.

(51) Int. Cl.
*A61F 9/007* (2006.01)
*A61M 1/00* (2006.01)

(52) U.S. Cl.
CPC ......... *A61F 9/00745* (2013.01); *A61M 1/774* (2021.05); *A61M 2210/0612* (2013.01)

(58) Field of Classification Search
CPC .................................................. F16K 31/1221
See application file for complete search history.

(56) References Cited

U.S. PATENT DOCUMENTS

| 3,948,478 | A | * | 4/1976 | Vind | F01D 17/26 |
| | | | | | 415/17 |
| 5,354,268 | A | | 10/1994 | Peterson et al. | |
| 7,044,156 | B2 | * | 5/2006 | Webster | E21B 43/01 |
| | | | | | 137/488 |
| 9,924,963 | B2 | * | 3/2018 | McDonell | A61F 9/00763 |
| 10,070,990 | B2 | * | 9/2018 | McDonell | A61F 9/00763 |
| 10,989,326 | B2 | * | 4/2021 | Rehhoff | F16K 31/124 |
| 11,642,243 | B2 | * | 5/2023 | Agahi | H01F 7/16 |
| | | | | | 606/107 |
| 2008/0105839 | A1 | | 5/2008 | Jennings et al. | |
| 2014/0171995 | A1 | | 6/2014 | McDonell | |
| 2016/0367735 | A1 | * | 12/2016 | Eddo | A61M 39/22 |
| 2021/0318155 | A1 | * | 10/2021 | Friedl | B05B 1/306 |

FOREIGN PATENT DOCUMENTS

CN          105202252 A  * 12/2015  ............. F16K 31/06

OTHER PUBLICATIONS

Translation of CN-105202252 (Year: 2015).*
CN-105202252A Translation (Year: 2015).*

* cited by examiner

*Primary Examiner* — Umashankar Venkatesan

(57) ABSTRACT

The present invention discloses a system comprising an actuation valve for receiving a first pressurized fluid, a piston in communication with the actuation valve, and a flow restrictor for controlling the flow of a second pressurized fluid from the piston. The flow restrictor may vent to ambient pressure and the piston may act as a pinch valve on at least one of an irrigation line.

20 Claims, 7 Drawing Sheets

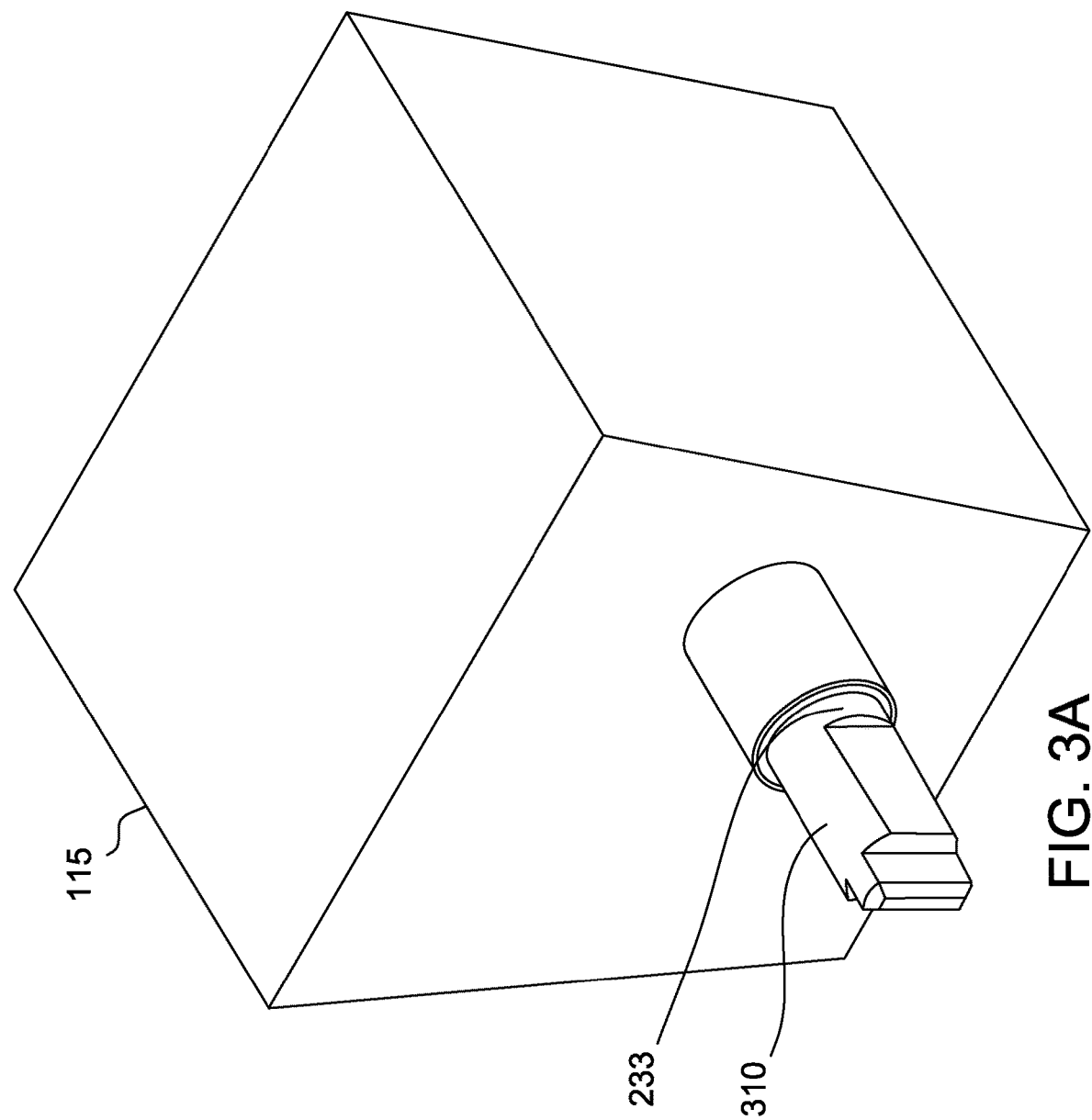

SYSTEM AND METHOD FOR EFFECTING WATER HAMMER IN SURGICAL SYSTEMS

CROSS-REFERENCE TO RELATED APPLICATIONS

This application claims the benefit under 35 U.S.C. § 119(e) of U.S. Provisional Patent Application No. 63/078,830, filed Sep. 15, 2020, which is incorporated herein by reference in its entirety.

BACKGROUND

Field of Technology

The present disclosure relates generally to phacoemulsification surgical systems. In particular, the present disclosure relates to reducing the effects of water hammer in certain fluidic systems within phacoemulsification systems including those system employing pinch valves.

Description of the Background

Cataracts affect more than 22 million Americans age 40 and older, and as the U.S. population ages, more than 53 million Americans are expected to have cataracts by the year 2030. Cataract surgery entails the removal of a lens of an eye that has developed clouding of the eye's natural lens, or opacification. As a result of opacification, light is unable to travel to the retina, thereby causing vision loss. Once vision becomes seriously impaired, cataract surgery is a viable option with a high level of success. During cataract surgery, a surgeon replaces the clouded lens with an intraocular lens (IOL).

Certain surgical procedures, such as phacoemulsification surgery, have been successfully employed in the treatment of certain ocular problems, such as cataracts. Phacoemulsification surgery utilizes a small corneal incision to insert the tip of at least one phacoemulsification handheld surgical implement, or handpiece, through the corneal incision. The handpiece includes a needle which is ultrasonically driven once placed within the incision to emulsify the eye lens, or to break the cataract into small pieces. The broken cataract pieces or emulsified eye lens may subsequently be removed using the same handpiece, or another handpiece, in a controlled manner. The surgeon may then insert a lens implant into the eye through the incision. The incision is allowed to heal, and the result for the patient is typically significantly improved eyesight.

During the phacoemulsification process for cataract removal, a consumable plastic cassette is generally used to collect effluent material. The disposable plastic cassette may consist of a tubing cassette which has flow paths for fluid and one or more valves to stop fluid flow or adjust fluid flow. In such phacoemulsification fluidics, there is a need for fluid to be valved off to stop fluid flow. To complicate matters, in a medical application such as phacoemulsification surgery, there cannot be a traditional direct in line valve.

Currently, companies use solenoid pinch valves, pneumatic pinch valves and rotary valves to shut off fluid flow in surgical system having small diameter tubing. Specifically, for solenoid and pneumatic pinch valves applications, the speed at which the irrigation valve opens can cause a water hammer effect on the fluid in the line and may cause a significant drop of pressure in the surgical field, namely the eye chamber, and may cause patient discomfort. Thus, there needs to be an apparatus and method to indirectly close off the fluid path through a consumable cassette while limiting any disruption to the pressure in the fluid line.

SUMMARY

Various embodiments recite a system for reducing water hammer effects in a phacoemulsification surgical system. The system may comprise an actuation valve for receiving a first pressurized fluid, a piston in communication with the actuation valve, and a flow restrictor for controlling the flow of a second pressurized fluid from the piston portion, which may include, for example, a piston, housing associated with the piston, and any associated sealing means. The flow restrictor may have a diameter of about 0.016 inches. The first pressurized fluid may be about 25 to about 50 psi apply a force to a return spring associated with the piston. The flow restrictor may vent to ambient pressure and the piston may act as a pinch valve on the irrigation line.

Various embodiments may also include a method for reducing water hammer effects in a phacoemulsification surgical system. The method may comprise actuating a linear actuator pinch valve to a first position with a first pressurized fluid and releasing a portion of the first pressurized fluid through a flow restrictor wherein the linear pinch valve moves to a second position. The flow restrictor may have a diameter of about 0.016 inches. The first pressurized fluid may about 25-50 psi and may comprise a balanced salt solution (BSS) fluid.

DESCRIPTION OF THE DRAWINGS

The accompanying drawings are included to provide a further understanding of the invention and are incorporated in and constitute a part of this specification. The drawings illustrate disclosed embodiments and/or aspects and, together with the description, serve to explain the principles of the invention, the scope of which is determined by the claims.

This disclosure is illustrated by way of example and not by way of limitation in the accompanying figure(s). The figure(s) may, alone or in combination, illustrate one or more embodiments of the disclosure. Elements illustrated in the figure(s) are not necessarily drawn to scale. Reference labels may be repeated among the figures to indicate corresponding or analogous elements.

FIGS. 3A and 3B are illustrations of pinch valve assembly in an exemplary embodiment;

DETAILED DESCRIPTION

It is to be understood that the figures and descriptions of the present disclosure have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

Embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

Figure 1A:
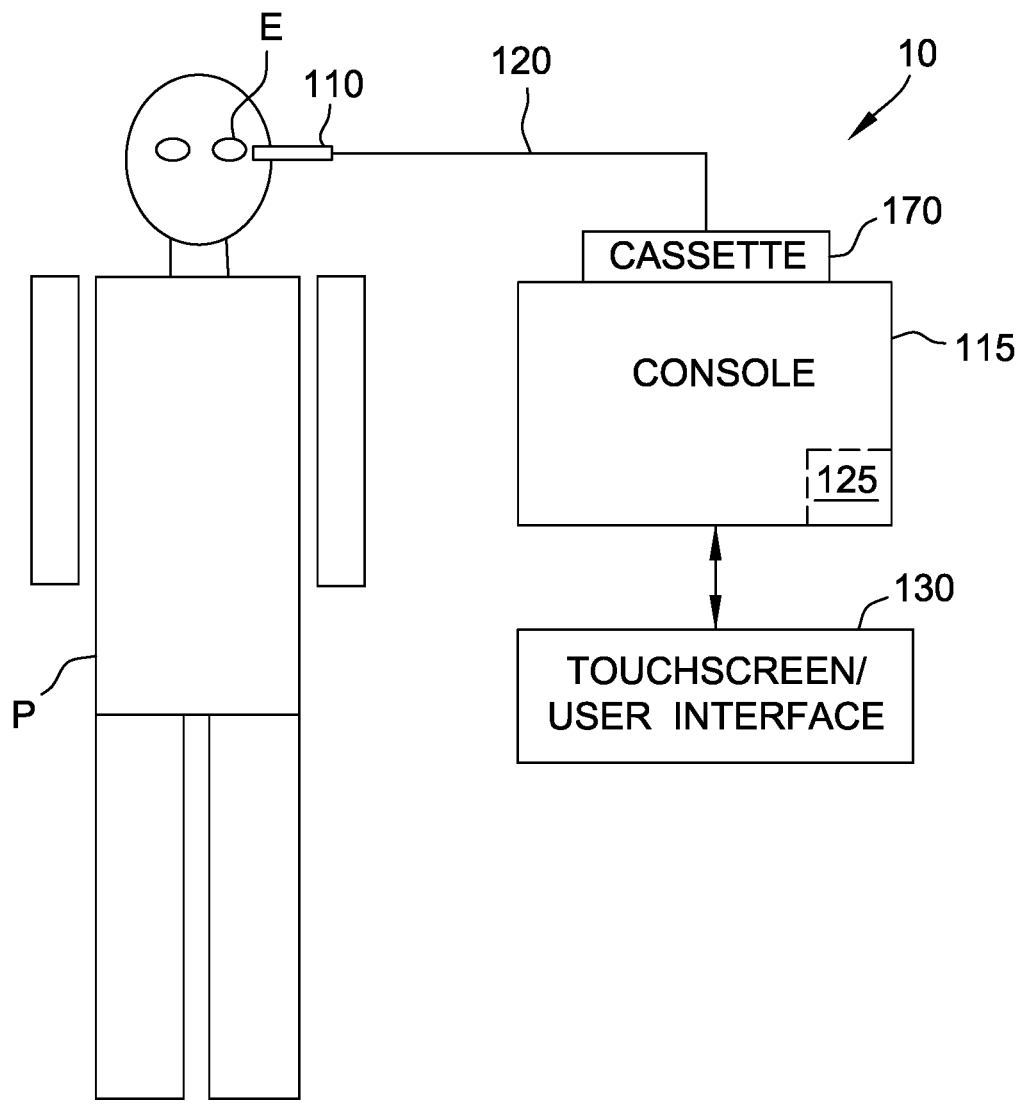
FIG. 1A is a schematic illustrating an eye treatment system in which a cassette is coupled to an eye treatment probe with an eye treatment console under one embodiment.

Referring now to FIG. 1A, an eye treatment system 10 for treating an eye E of a patient P generally includes an eye treatment probe handpiece 110 coupled with a console 115 by a cassette 170. Handpiece 110 generally includes a handle for manually manipulating and supporting an insertable probe tip. The probe tip has a distal end which is insertable into the eye, with one or more lumens in the probe tip allowing irrigation fluid to flow from console 115 and/or cassette 170 into the eye. Aspiration fluid may also be withdrawn through a lumen of the probe tip, with console 115 and cassette 170 generally including a vacuum aspiration source, a positive displacement aspiration pump, or both to help withdraw and control a flow of surgical fluids into and out of eye E. As the surgical fluids may include biological materials that should not be transferred between patients, cassette 170 will often comprise a sterilizable (or alternatively, disposable) structure, with the surgical fluids being transmitted through flexible conduits 120 of cassette 170 that avoid direct contact in between those fluids and the components of console 115.

When a distal end of the probe tip of handpiece 110 is inserted into an eye E, for example, for removal of a lens of a patient P with cataracts, an electrical conductor and/or pneumatic line (not shown) may supply energy from console 115 to an ultrasound transmitter of handpiece 110, a cutter mechanism, or the like. Alternatively, handpiece 110 may be configured as an irrigation/aspiration (I/A) and/or vitrectomy handpiece. Also, the ultrasonic transmitter may be replaced by other means for emulsifying a lens, such as a high energy laser beam. The ultrasound energy from handpiece 110 helps to fragment the tissue of the lens, which can then be drawn into a port of the tip by aspiration flow. So as to balance the volume of material removed by the aspiration flow, an irrigation flow through handpiece 110 (or a separate probe structure) may also be provided, with both the aspiration and irrigation flows being controlled by console 115.

To avoid cross-contamination between patients without incurring excessive expenditures for each procedure, cassette 170 and its flexible conduits 120 may be disposable. However, the flexible conduit or tubing may be disposable, with the cassette body and/or other structures of the cassette being sterilizable. Cassette 170 may be configured to interface with reusable components of console 115, including, but not limited to, peristaltic pump rollers, a Venturi or other vacuum source, a controller 125, and/or the like.

Console 115 may include controller 125, which may include an embedded microcontroller and/or many of the components common to a personal computer, such as a processor, data bus, a memory, input and/or output devices (including a user interface 130 (e.g. touch screen, graphical user interface (GUI), etc.), and the like. Controller 125 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 125 may have (or be coupled with) a recording media reader, or the code may be transmitted to controller 125 by a network connection such as an internet, an intranet, an ethernet, a wireless network, or the like. Along with programming code, controller 125 may include stored data for implementing the methods described herein and may generate and/or store data that records parameters corresponding to the treatment of one or more patients.

Figure 1B:
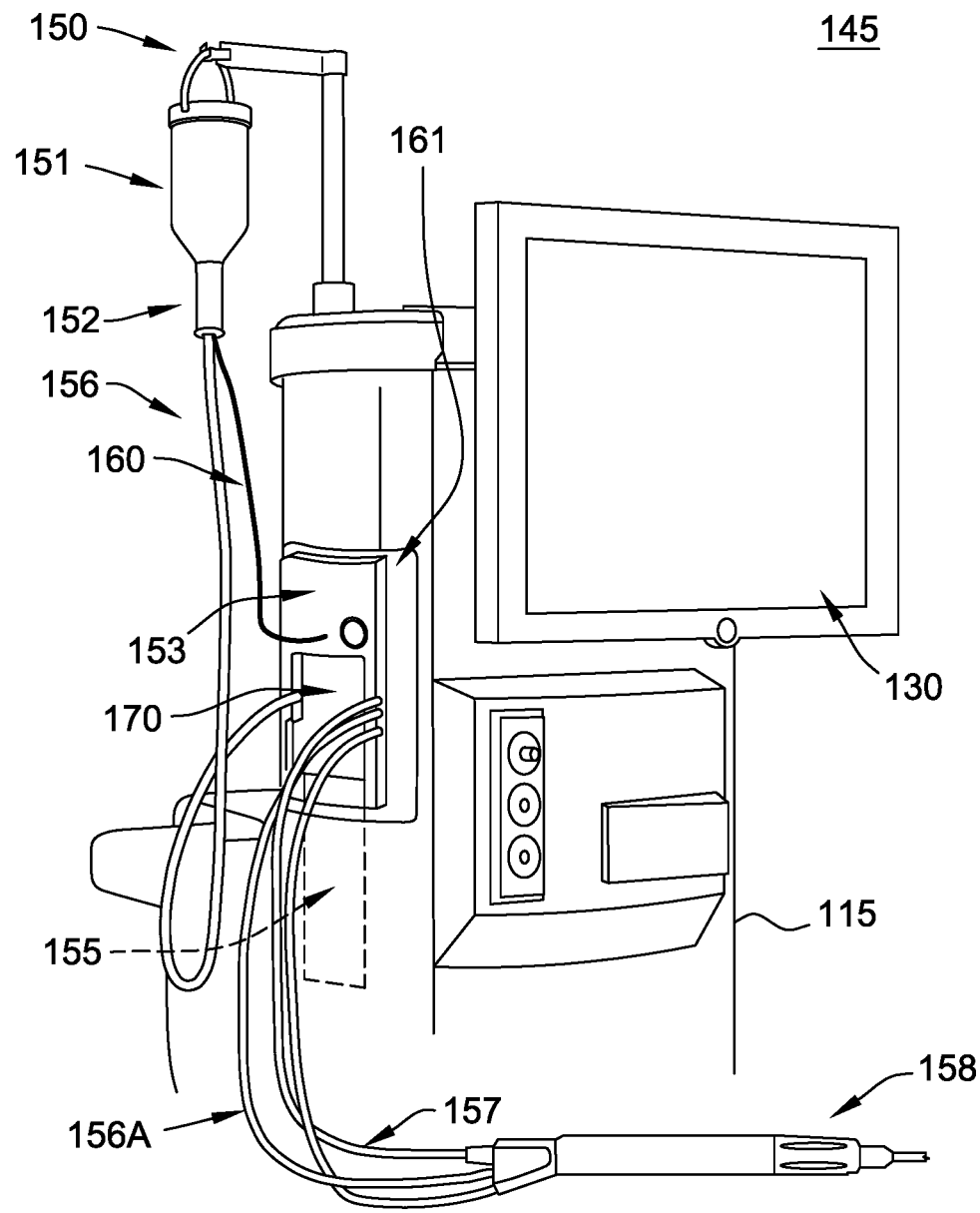
FIG. 1B is a schematic illustrating a surgical eye treatment console under another exemplary embodiment.

Referring now to FIG. 1B, a simplified surgical system 145 comprising console 115 is illustrated, where a fluid path may be demonstrated under an exemplary embodiment. In this example, an irrigation source 151 may be configured as a bottle or bag hanging from an IV pole hanger 150. It is understood by those skilled in the art that, while an integrated IV pole is illustrated, other configurations, utilizing standalone/static IV poles, pressurized infusion sources, and/or other suitable configurations, are contemplated by the present disclosure.

An exemplary irrigation path for fluid may be realized via tubing cassette 170 coupled with cassette tubing interface 153, which receives fluid from irrigation source 151 via drip chamber 152. Irrigation line 156A and aspiration line 157 are coupled to handpiece 158. Irrigation fluid may flow from drip chamber 152 through the irrigation tubing 156 into tubing cassette 170. Irrigation fluid may then flow from the tubing cassette through handpiece irrigation line 156A which may be coupled to an irrigation port on handpiece 158. Aspirated fluid may flow from the eye through the handpiece aspiration line 157 back to tubing cassette 170 and into a waste collection bag 155. Cassette 170 may be removably engaged with console 115 in cassette receptacle 161 which may be shaped to accept only a cassette compatible with console 115. A touch screen display 130 may be provided to display system operation conditions and parameters, and may include a user interface (e.g., touch screen, keyboard, track ball, mouse, etc.—see touchscreen/user interface 130 of FIG. 1A) for entering data and/or instructions to the system of FIG. 1B.

Figure 2:
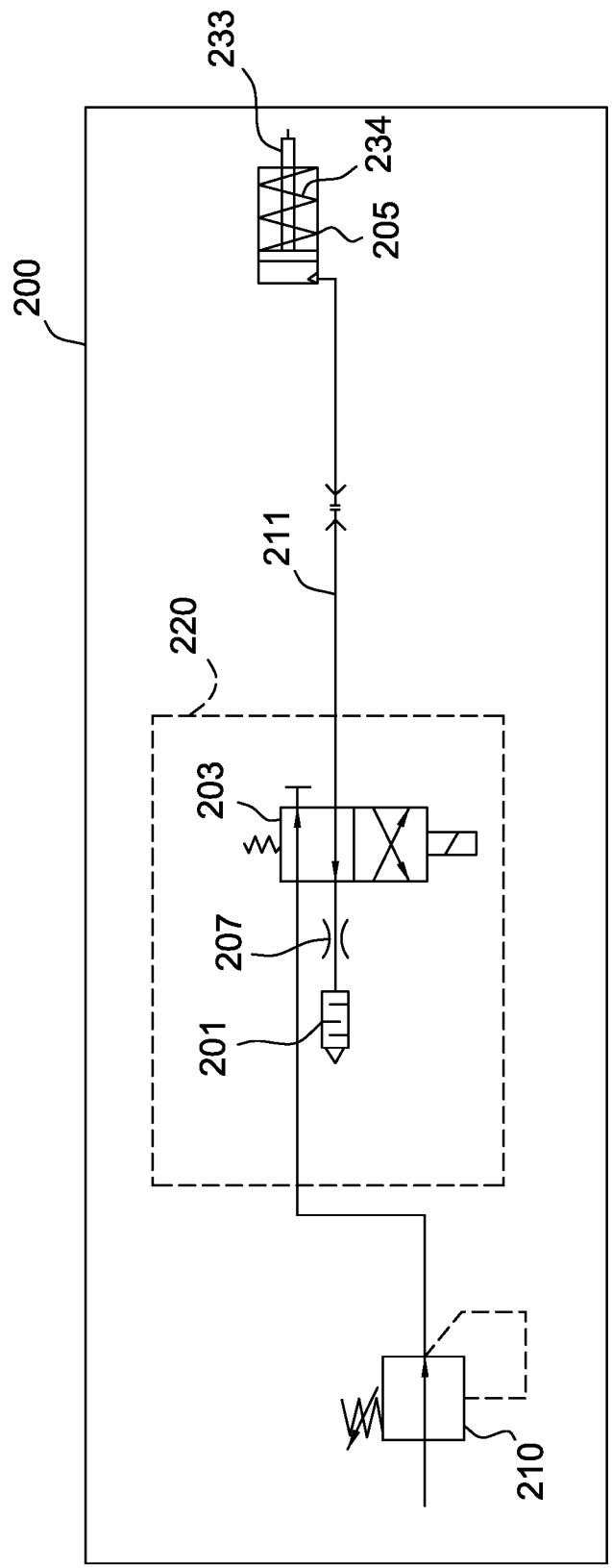
FIG. 2 is a schematic illustrating a portion of the pinch valve system in an exemplary embodiment.

FIG. 2 is a schematic illustrating a portion of the pinch valve system in an exemplary embodiment. Pinch valve system 200 may comprise at least one pinch valve and is housed in console 115 and controlled by the console and/or through the user interface 130. A pinch valve associated with the pinch valve system 200 may be positioned to act on at least one portion of tubing associated with a cassette 170 attached to the console 115.

Pinch valve system 200 may be pneumatic and may include at least one piston portion 205 associated with an irrigation line. The piston portion may comprise at least one pneumatic piston, which may, preferably, comprise a pinch valve. The piston portion may also be fluidly associated with an activation assembly which may control the flow of compressed fluid to a piston portion. For example, activation assembly 220 may be fluidly connected to piston portion 205 by line 211.

The irrigation activation assembly 220 may comprise an irrigation activation valve 203 and at least one vent 201. Irrigation activation valve 203 may receive a compressed fluid from pneumatic fluid source 210 and controls the delivery of the compressed fluid to piston portion 205. Control of irrigation activation valve 203 may be through console 115 and may be responsive to the user of the console and/or to automated console controls. Vent 201 may provide venting to atmosphere and may be fluidly connected to irrigation activation valve 203 and may provide both pressure regulation for received fluid pressure and venting which may be used to regulate both received fluid pressure(s) and to release pressure exerted on piston portion 205.

In an embodiment of the present invention, fluid delivered from pneumatic fluid source 210, preferably in the form of air, has a pressure greater than atmosphere and may, preferably, have a pressure of about 25-50 psi. Pneumatic fluid source 210 may have a reservoir and/or pump associated therewith. The pressurized fluid is communicated to activation valve 203 which, upon activation, communicates a portion of the received fluid to piston portion 205. The received pressurized fluid may act on piston 233. A return spring 234 is associated with piston 233 and may provide resistance and/or tension to the lateral movement of piston 233. The pressure of the pneumatic fluid used in pinch valve system 200 may vary and may be calibrated to the spring's constant value k. Such calibrating of pressure may allow for a high degree of control over the speed of actuation of piston portion 205.

For example, the piston 233 of piston portion 205 may be fully actuated instantaneously in response to an applied fluid pressure to act on, for example, a portion of tubing to stop fluid flow in the tubing, and may be slowly released by bleeding off the supplied fluid pressure through, for example, vent 201. This type of control over the releasing of the piston and the allowing of continued fluid flow in the tubing provides a reduction in water hammer effects down flow from the piston, or more specifically, between the pinch valve created by the piston acting on the tubing and the terminus point for fluid flowing in the tubing (i.e., the surgical site).

Control over the speed of actuation of the pneumatically actuated piston 233 of the present invention may be controlled by the delivery of pressurized fluid and the release or bleeding of fluid pressure on piston portion 205. Using compressed air as the fluid, the present invention may provide any value of pressure from pneumatic fluid source 210 to either activation valve 203, such as, for example, air pressurized to at least 30 psi. Each activation valve may also release the pressure on the piston through a flow restrictor (207) associated with the vent (201, 208). For example, flow restrictor 207 may be in communication with activation valve 203 and vent 201 and may have a diameter of less the 0.02 inches and may, preferably, have a diameter of 0.016 inches to reduce the speed and turbulence of releasing the pressure on piston portion 205.

Figure 3B:
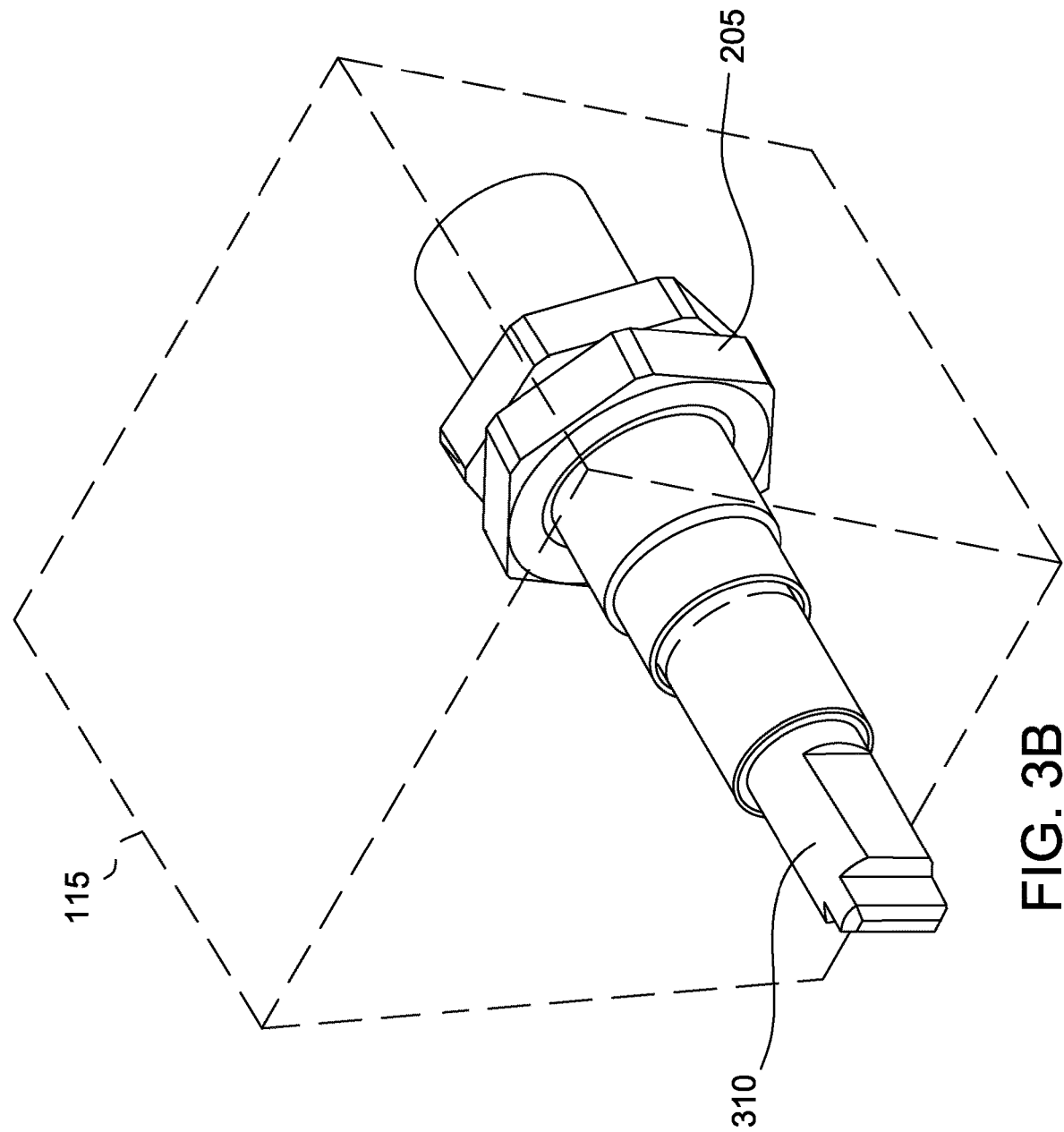
Figure 3C:
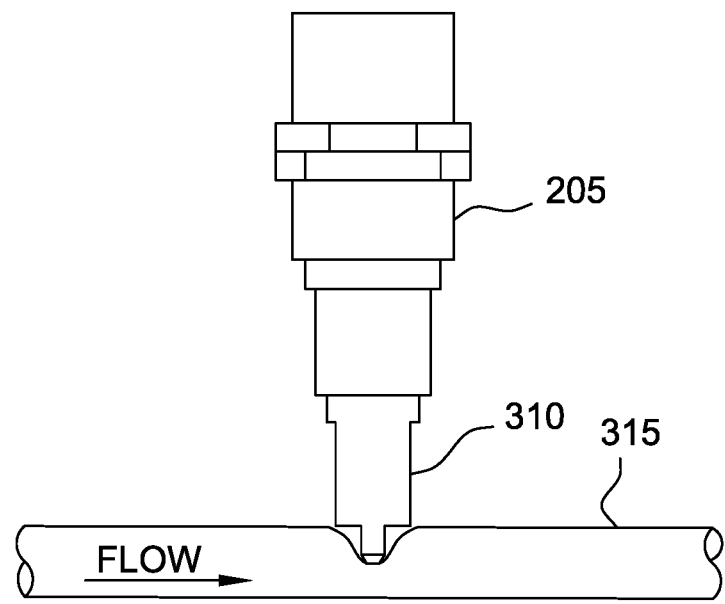
FIGS. 3C and 3D are illustrations of pinch valve assembly in an exemplary embodiment.
Figure 3D:
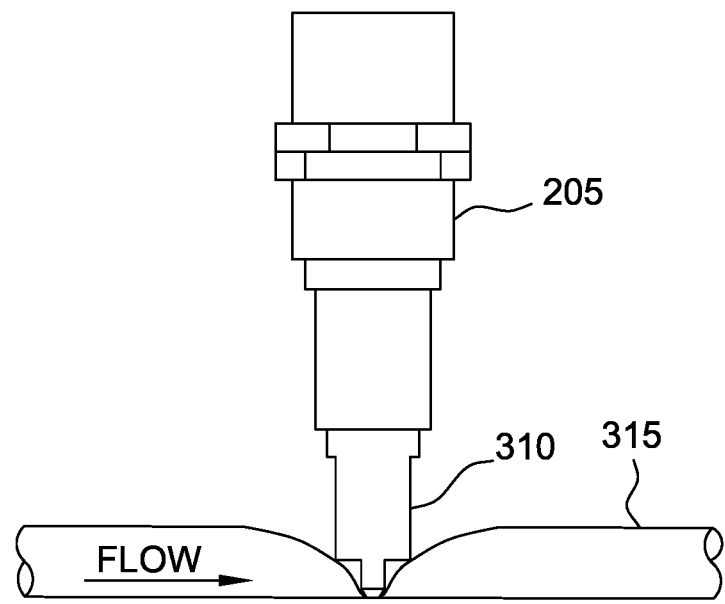

As illustrated in FIGS. 3A and 3B, console 115 may comprise piston portion 205, with at least a portion of piston portion 205, e.g. a portion of piston 233, extending beyond a surface of console 115 or beyond a surface of or into a portion of a cassette receptacle 161 of the console 115. The pinch valve portion 310 may form a part of piston 233 and may be positioned to interact with tubing outside of the console 115, such as, for example, in a surgical cassette removably associated cassette receptacle 161 of console 115. For example, as illustrated in FIG. 3C, pinch valve portion 310 associated with piston portion 205 may come in contact with and partially reduce flow in tubing 315. When piston 233 is fully actuated, pinch valve portion 310 may, as illustrated in FIG. 3D, fully inhibit fluid flow in tubing 315 as pinch valve portion 310 may substantially and/or fully stop flow of fluids in tubing 315.

The tip of pinch valve portion 310 may be of any shape which may allow the pinch valve portion 310 to compress tubing 315 to affect the flow of fluid in tubing 315 without damaging the tubing. The tubing may be resident in a surgical cassette and may provide a rigid surface on which tubing 315 may reside and against which pinch valve portion 310 may actuate against. As would be appreciated by those skilled in the art, the stiffness of the tubing and tip of the pinch valve portion 310 may be varied in relation to the viscosity and pressure of the fluid being transported in tubing 315.

Figure 4:
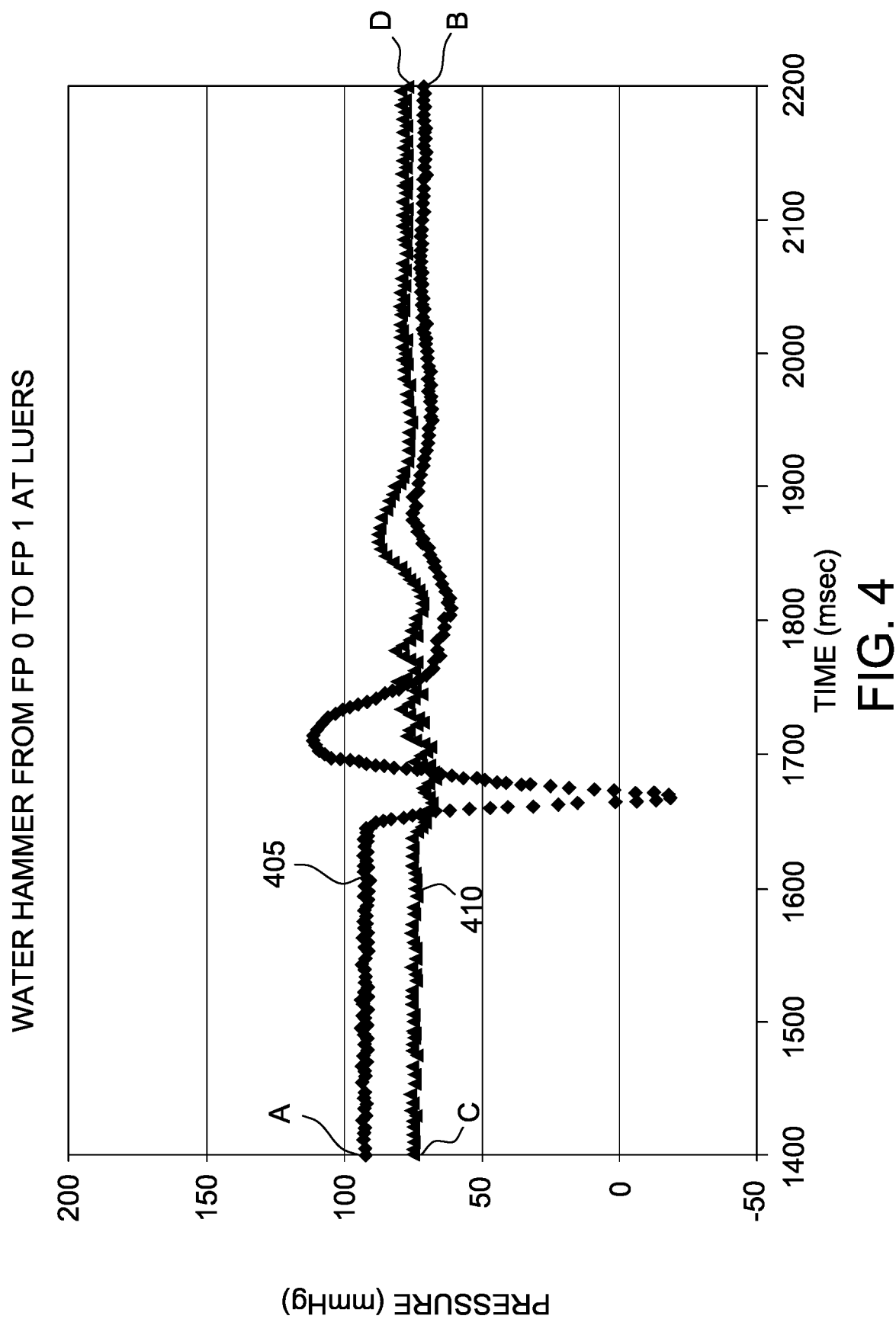
FIG. 4 is a graphical illustration of measured pressure in an exemplary embodiment.

As illustrated in FIG. 4, the use of a pneumatically driven linear actuator as described above greatly reduces the variance in fluid pressure changes that may result from a surge in fluid pressure if fluid flow is released in too abrupt a manner. More specifically, as demonstrated by the irrigation fluid pressure measured at the point of use, the opening of the pressurized irrigation line using a solenoid valve, for example, as illustrated by line 405, may result in a variety of pressure variations versus the target pressure B. The quick release of the pressurized fluid first results in a larger than desired pressure A which proceeds a follow-on water hammer effect measured between time 1600 and about 1900, until the pressure returns to nearly about the target pressure of B. Using a pneumatic linear actuator, as illustrated by line 410, the pressure registered immediately following opening the irrigation line may be controlled to the pressure of C. This greater control over pressure and volume greatly diminishes any water hammer between time 1600 and about 1900 and allows the first measured pressure C to be nearly that of the operational target pressure B.

Those of skill in the art will appreciate that the herein described apparatuses, devices, systems and methods are susceptible to various modifications and alternative constructions. There is no intention to limit the scope of the invention to the specific constructions described herein. Rather, the herein described systems and methods are intended to cover all modifications, alternative constructions, and equivalents falling within the scope and spirit of the disclosure, any appended claims and any equivalents thereto.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather are to be accorded the widest scope consistent with the principles and novel features disclosed herein.

What is claimed is:

1. A system for controlling fluid flow through a flexible conduit tube to reduce water hammer effects in a phacoemulsification surgical system, comprising:
   an actuation valve for receiving pressurized fluid;
   a piston portion in communication with the actuation valve for receiving at least a portion of the pressurized fluid, wherein the piston portion includes a piston configured to be moveable between an extended position and a retracted position, wherein the piston is configured to compress the flexible conduit in the extended position to prevent or reduce fluid flow through the flexible conduit, and wherein the piston is configured to disengage from the flexible conduit in the retracted position to permit fluid flow through the flexible conduit;
   a flow restrictor for controlling the flow of the pressurized fluid received from the piston portion; and
   a vent for releasing pressure applied to the piston portion by the pressurized fluid to atmosphere
   wherein the actuation valve is configured to control speed of actuation of the piston portion.

2. The system of claim 1, wherein the flow restrictor has a diameter of less than about 0.020 inches or less than about 0.080 inches.

3. The system of claim 1, wherein the flow restrictor has a diameter of about 0.016 inches or about 0.060 inches.

4. The system of claim 1, further comprising a fluid source configured to provide the pressurized fluid to the actuation valve.

5. The system of claim 1, wherein the actuation valve is configured to regulate the pressure of the pressurized fluid for controlling the speed of the actuation of the piston between the extended position and the retracted position.

6. The system of claim 1, wherein the pressure of the pressurized fluid is selected from the range of 25 psi to 50 psi.

7. The system of claim 1, wherein the received pressurized fluid is less than about 50 psi.

8. The system of claim 1, wherein the pressurized fluid causes a force to be applied to a return spring associated with the piston portion.

9. The system of claim 1, wherein the flow restrictor is configured to vent to ambient pressure.

10. The system of claim 1, wherein the actuation valve is controlled by a surgical console, wherein the surgical console is in communication with a graphical user interface.

11. The system of claim 1, wherein the piston portion comprises a pinch valve, and wherein the tube comprises an irrigation line.

12. A method for controlling fluid flow through a flexible conduit to reduce water hammer effects in a phacoemulsification surgical system, comprising:
   actuating a piston between an extended position and a retracted position using a pressurized fluid, wherein the piston compresses the flexible conduit in the extended position to prevent or reduce fluid flow through the flexible conduit, and wherein the piston disengages from the flexible conduit in the retracted position to permit fluid flow through the flexible conduit; and
   releasing a portion of the pressurized fluid through a flow restrictor; and
   wherein the actuating is performed so as to control speed of actuation of the piston.

13. The method of claim 12, wherein the flow restrictor has a diameter of less than about 0.020 inches or less than about 0.080 inches.

14. The method of claim 12, wherein the flow restrictor has a diameter of about 0.016 inches or about 0.060 inches.

15. The method of claim 12, further comprising providing the pressurized fluid to actuate the piston.

16. The method of claim 12, wherein the pressurized fluid is about 30 psi.

17. The method of claim 12, wherein the released portion of the pressurized fluid is less than about 30 psi.

18. The method of claim 12, wherein the flow restrictor vents to ambient pressure.

19. The method of claim 12, wherein the piston comprises a pinch valve, and wherein the tube comprises at least one irrigation line.

20. The method of claim 12, further comprising regulating the pressure of the pressurized fluid to control the speed of the actuation of the piston between the extended position and the retracted position.

* * * * *